United States Patent [19]
Honjo et al.

[11] Patent Number: 5,563,048
[45] Date of Patent: Oct. 8, 1996

[54] HUMAN STROMAL DERIVED FACTOR 1α AND 1β, AND DNAS ENCODING THE SAME

[75] Inventors: Tasuku Honjo; Michio Shirozu, both of Kyoto; Hideaki Tada, Osaka, all of Japan

[73] Assignee: Ono Pharmaceutical Co., Ltd., Osaka, Japan

[21] Appl. No.: 323,084

[22] Filed: Oct. 14, 1994

[30] Foreign Application Priority Data

Oct. 14, 1993 [JP] Japan ................................ 5-280505

[51] Int. Cl.$^6$ .......................... C12N 15/12; C07K 14/475
[52] U.S. Cl. .................. 435/69.1; 435/172.3; 435/240.1; 435/252.3; 435/320.1; 536/23.1; 536/23.5; 935/11; 935/22; 935/52; 935/66
[58] Field of Search ..................... 536/23.1, 23.5; 435/69.1, 172.3, 240.2, 240.3, 252.3, 320.1, 70.1; 530/300; 935/4, 11, 22, 52, 70

[56] References Cited

FOREIGN PATENT DOCUMENTS 0607054  1/1994  European Pat. Off. .

OTHER PUBLICATIONS

Weissenbach et al, 1980, Proc. Natl. Acad Sci., vol. 77, No. 12, pp. 7152–7156.
Derynck et al. 1990, Biochemistry, vol. 29 pp. 10225–10233.
Nagasawa et al., "Molecular cloning and structure of a pre-B-cell growth-stimulating factor", Proc. Natl. Acad. Sci. USA, vol. 91, pp. 2305–2309, Mar. 1994.
Tashiro et al., "Signal Sequence Trap: A Cloning Strategy for Secreted Proteins and Type I Membrane Proteins", Science, vol. 261, Jul. 30, 1993 pp. 600–603.

*Primary Examiner*—Stephen G. Walsh
*Assistant Examiner*—Prema Mertz
*Attorney, Agent, or Firm*—Sughrue, Mion, Zinn, Macpeak & Seas

[57] ABSTRACT

The Stromal Derived Factor-1α (SDF-1α) and Stromal Derived Factor-1β (SDF-1β) polypeptides of the present invention are produced and secreted in pro-B cells, so they may be used for diseases relating to undergrown or abnormal proliferation of hematopoietic cells, neuronal enhancement or depression, immunological enhancement and depression, for example, inflammatory diseases (rheumatoid arthritis, ulcerative colitis etc.), hematopoietic stemcytopenia after bone marrow transplantation, leukocytopenia, thrombocytopenia, B lymphopenia and T lymphopenia after chemotherapy, anemia, infectious diseases, cancer, leukocytosis, AIDS, neurodegenerative diseases (Alzheimer, multiple sclerosis etc.), prevention or treatment of neuronal injury, prevention or treatment of disorder of bone metabolism (osteoporosis etc.) or tissue repair. The DNAs of the present invention may be utilized as important and essential templates in preparing the polypeptides of the present invention which are expected to possess various uses or for diagnosis of and in the treatment of gene diseases.

12 Claims, 1 Drawing Sheet

BOX INDICATES OPEN
READING FRAME 300 bp

BOX INDICATES OPEN
READING FRAME 500 bp pUSCSRαML2 Vector

SEQUENCE LISTING ( 1 ) GENERAL INFORMATION:

( i i i ) NUMBER OF SEQUENCES: 20

( 2 ) INFORMATION FOR SEQ ID NO:1:

( i ) SEQUENCE CHARACTERISTICS:
( A ) LENGTH: 89 amino acids
( B ) TYPE: amino acid
( D ) TOPOLOGY: linear ( i i ) MOLECULE TYPE: protein ( x i ) SEQUENCE DESCRIPTION: SEQ ID NO:1:

Met Asn Ala Lys Val Val Val Val Leu Val Leu Val Leu Thr Ala Leu
 1               5                  10                  15

Cys Leu Ser Asp Gly Lys Pro Val Ser Leu Ser Tyr Arg Cys Pro Cys

|  | 20 |  |  |  |  | 25 |  |  |  |  | 30 |  |  |  |
|---|---|---|---|---|---|---|---|---|---|---|---|---|---|---|
| Arg | Phe | Phe<br>35 | Glu | Ser | His | Val | Ala<br>40 | Arg | Ala | Asn | Val | Lys<br>45 | His | Leu | Lys |
| Ile | Leu<br>50 | Asn | Thr | Pro | Asn | Cys<br>55 | Ala | Leu | Gln | Ile | Val<br>60 | Ala | Arg | Leu | Lys |
| Asn<br>65 | Asn | Asn | Arg | Gln | Val<br>70 | Cys | Ile | Asp | Pro | Lys<br>75 | Leu | Lys | Trp | Ile | Gln<br>80 |
| Glu | Tyr | Leu | Glu | Lys<br>85 | Ala | Leu | Asn | Lys |

( 2 ) INFORMATION FOR SEQ ID NO:2:

( i ) SEQUENCE CHARACTERISTICS:
        ( A ) LENGTH: 267 base pairs
        ( B ) TYPE: nucleic acid
        ( C ) STRANDEDNESS: single
        ( D ) TOPOLOGY: linear ( i i ) MOLECULE TYPE: cDNA to mRNA ( x i ) SEQUENCE DESCRIPTION: SEQ ID NO:2:

| ATGAACGCCA | AGGTCGTGGT | CGTGCTGGTC | CTCGTGCTGA | CCGCGCTCTG | CCTCAGCGAC | 60 |
| ---------- | ---------- | ---------- | ---------- | ---------- | ---------- | --- |
| GGGAAGCCCG | TCAGCCTGAG | CTACAGATGC | CCATGCCGAT | TCTTCGAAAG | CCATGTTGCC | 120 |
| AGAGCCAACG | TCAAGCATCT | CAAAATTCTC | AACACTCCAA | ACTGTGCCCT | TCAGATTGTA | 180 |
| GCCCGGCTGA | AGAACAACAA | CAGACAAGTG | TGCATTGACC | CGAAGCTAAA | GTGGATTCAG | 240 |
| GAGTACCTGG | AGAAAGCTTT | AAACAAG |  |  |  | 267 |

( 2 ) INFORMATION FOR SEQ ID NO:3:

( i ) SEQUENCE CHARACTERISTICS:
        ( A ) LENGTH: 1856 base pairs
        ( B ) TYPE: nucleic acid
        ( C ) STRANDEDNESS: single
        ( D ) TOPOLOGY: linear ( i i ) MOLECULE TYPE: cDNA to mRNA ( x i ) SEQUENCE DESCRIPTION: SEQ ID NO:3:

| TCTCCGTCAG | CCGCATTGCC | CGCTCGGCGT | CCGGCCCCCG | ACCCGTGCTC | GTCCGCCCGC | 60 |
| ---------- | ---------- | ---------- | ---------- | ---------- | ---------- | --- |
| CCGCCCGCCC | GCCCGCGCCA | TGAACGCCAA | GGTCGTGGTC | GTGCTGGTCC | TCGTGCTGAC | 120 |
| CGCGCTCTGC | CTCAGCGACG | GGAAGCCCGT | CAGCCTGAGC | TACAGATGCC | CATGCCGATT | 180 |
| CTTCGAAAGC | CATGTTGCCA | GAGCCAACGT | CAAGCATCTC | AAAATTCTCA | ACACTCCAAA | 240 |
| CTGTGCCCTT | CAGATTGTAG | CCCGGCTGAA | GAACAACAAC | AGACAAGTGT | GCATTGACCC | 300 |
| GAAGCTAAAG | TGGATTCAGG | AGTACCTGGA | GAAAGCTTTA | AACAAGTAAG | CACAACAGCC | 360 |
| AAAAAGGACT | TTCCGCTAGA | CCCACTCGAG | GAAAACTAAA | ACCTTGTGAG | AGATGAAAGG | 420 |
| GCAAAGACGT | GGGGGAGGGG | GCCTTAACCA | TGAGGACCAG | GTGTGTGTGT | GGGGTGGGCA | 480 |
| CATTGATCTG | GGATCGGGCC | TGAGGTTTGC | AGCATTTAGA | CCCTGCATTT | ATAGCATACG | 540 |
| GTATGATATT | GCAGCTTATA | TTCATCCATG | CCCTGTACCT | GTGCACGTTG | AACTTTTAT | 600 |
| TACTGGGGTT | TTTCTAAGAA | AGAAATTGTA | TTATCAACAG | CATTTTCAAG | CAGTTAGTTC | 660 |
| CTTCATGATC | ATCACAATCA | TCATCATTCT | CATTCTCATT | TTTAAATCA | ACGAGTACTT | 720 |
| CAAGATCTGA | ATTTGGCTTG | TTTGGAGCAT | CTCCTCTGCT | CCCCTGGGGA | GTCTGGGCAC | 780 |
| AGTCAGGTGG | TGGCTTAACA | GGGAGCTGGA | AAAAGTGTCC | TTTCTTCAGA | CACTGAGGCT | 840 |
| CCCGCAGCAG | CGCCCCTCCC | AAGAGGAAGG | CCTCTGTGGC | ACTCAGATAC | CGACTGGGGC | 900 |

-continued

| | | | | | |
|---|---|---|---|---|---|
| TGGGGCGCCG | CCACTGCCTT | CACCTCCTCT | TTCAAACCTC | AGTGATTGGC | TCTGTGGGCT | 960 |
| CCATGTAGAA | GCCACTATTA | CTGGGACTGT | CTCAGAGACC | CCTCTCCCAG | CTATTCCTAC | 1020 |
| TCTCTCCCCG | ACTCCGAGAG | CATGCTTAAT | CTTGCTTCTG | CTTCTCATTT | CTGTAGCCTG | 1080 |
| ATCAGCGCCG | CACCAGCCGG | GAAGAGGGTG | ATTGCTGGGG | CTCGTGCCCT | GCATCCCTCT | 1140 |
| CCTCCCAGGG | CCTGCCCCAC | AGCTCGGGCC | CTCTGTGAGA | TCCGTCTTTG | GCCTCCTCCA | 1200 |
| GAATGGAGCT | GGCCCTCTCC | TGGGGATGTG | TAATGGTCCC | CCTGCTTACC | CGCAAAAGAC | 1260 |
| AAGTCTTTAC | AGAATCAAAT | GCAATTTTAA | ATCTGAGAGC | TCGCTTGAGT | GACTGGGTTT | 1320 |
| GTGATTGCCT | CTGAAGCCTA | TGTATGCCAT | GGAGGCACTA | ACAAACTCTG | AGGTTTCCGA | 1380 |
| AATCAGAAGC | GAAAAAATCA | GTGAATAAAC | CATCATCTTG | CCACTACCCC | CTCCTGAAGC | 1440 |
| CACAGCAGGG | GTTCAGGTTC | CAATCAGAAC | TGTTGGCAAG | GTGACATTTC | CATGCATAGA | 1500 |
| TGCGATCCAC | AGAAGGTCCT | GGTGGTATTT | GTAACTTTTT | GCAAGGCATT | TTTTTATATA | 1560 |
| TATTTTTGTG | CACATTTTTT | TTTACGATTC | TTTAGAAAAC | AAATGTATTT | CAAAATATAT | 1620 |
| TTATAGTCGA | ACAAGTCATA | TATATGAATG | AGAGCCATAT | GAATGTCAGT | AGTTTATACT | 1680 |
| TCTCTATTAT | CTCAAACTAC | TGGCAATTTG | TAAAGAAATA | TATATGATAT | ATAAATGTGA | 1740 |
| TTGCAGCTTT | TCAATGTTAG | CCACAGTGTA | TTTTTTCACT | TGTACTAAAA | TTGTATCAAA | 1800 |
| TGTGACATTA | TATGCACTAG | CAATAAAATG | CTAATTGTTT | CATGGTAAAA | AAAAAA | 1856 |

( 2 ) INFORMATION FOR SEQ ID NO:4:

( i ) SEQUENCE CHARACTERISTICS:
        ( A ) LENGTH: 1856 base pairs
        ( B ) TYPE: nucleic acid
        ( C ) STRANDEDNESS: single
        ( D ) TOPOLOGY: linear ( i i ) MOLECULE TYPE: cDNA to mRNA ( v i ) ORIGINAL SOURCE:
        ( A ) ORGANISM: Homo sapiens
        ( H ) CELL LINE: FLEB14

( i x ) FEATURE:
        ( A ) NAME/KEY: CDS
        ( B ) LOCATION: 80..349
        ( C ) IDENTIFICATION METHOD: by similarity to some other pattern ( i x ) FEATURE:
        ( A ) NAME/KEY: sig_peptide
        ( B ) LOCATION: 80..142
        ( C ) IDENTIFICATION METHOD: by similarity with known sequence
                or to an established consensus ( i x ) FEATURE:
        ( A ) NAME/KEY: mat_peptide
        ( B ) LOCATION: 143..346
        ( C ) IDENTIFICATION METHOD: by similarity with known sequence
                or to an established consensus ( x i ) SEQUENCE DESCRIPTION: SEQ ID NO:4:

```
TCTCCGTCAG  CCGCATTGCC  CGCTCGGCGT  CCGGCCCCCG  ACCCGTGCTC  GTCCGCCCGC        60

CCGCCCGCCC  GCCCGCGCC  ATG  AAC  GCC  AAG  GTC  GTG  GTC  GTG  CTG  GTC  CTC   112
                      Met  Asn  Ala  Lys  Val  Val  Val  Val  Leu  Val  Leu
                      -21  -20                     -15

GTG  CTG  ACC  GCG  CTC  TGC  CTC  AGC  GAC  GGG  AAG  CCC  GTC  AGC  CTG  AGC  160
Val  Leu  Thr  Ala  Leu  Cys  Leu  Ser  Asp  Gly  Lys  Pro  Val  Ser  Leu  Ser
-10                 -5                   1                    5

TAC  AGA  TGC  CCA  TGC  CGA  TTC  TTC  GAA  AGC  CAT  GTT  GCC  AGA  GCC  AAC   208
Tyr  Arg  Cys  Pro  Cys  Arg  Phe  Phe  Glu  Ser  His  Val  Ala  Arg  Ala  Asn
               10                  15                       20
```

```
GTC  AAG  CAT  CTC  AAA  ATT  CTC  AAC  ACT  CCA  AAC  TGT  GCC  CTT  CAG  ATT     256
Val  Lys  His  Leu  Lys  Ile  Leu  Asn  Thr  Pro  Asn  Cys  Ala  Leu  Gln  Ile
          25                        30                  35

GTA  GCC  CGG  CTG  AAG  AAC  AAC  AAC  AGA  CAA  GTG  TGC  ATT  GAC  CCG  AAG     304
Val  Ala  Arg  Leu  Lys  Asn  Asn  Asn  Arg  Gln  Val  Cys  Ile  Asp  Pro  Lys
          40                        45                  50

CTA  AAG  TGG  ATT  CAG  GAG  TAC  CTG  GAG  AAA  GCT  TTA  AAC  AAG  TAAGCACAAC    356
Leu  Lys  Trp  Ile  Gln  Glu  Tyr  Leu  Glu  Lys  Ala  Leu  Asn  Lys
55                        60                  65
```

| | | | | |
|---|---|---|---|---|
| AGCCAAAAAG | GACTTCCGC | TAGACCCACT | CGAGGAAAAC | TAAAACCTTG  TGAGAGATGA | 416 |
| AAGGGCAAAG | ACGTGGGGGA | GGGGGCCTTA | ACCATGAGGA | CCAGGTGTGT  GTGTGGGGTG | 476 |
| GGCACATTGA | TCTGGGATCG | GGCCTGAGGT | TTGCAGCATT | TAGACCCTGC  ATTTATAGCA | 536 |
| TACGGTATGA | TATTGCAGCT | TATATTCATC | CATGCCCTGT | ACCTGTGCAC  GTTGGAACTT | 596 |
| TTATTACTGG | GGTTTTTCTA | AGAAAGAAAT | TGTATTATCA | ACAGCATTTT  CAAGCAGTTA | 656 |
| GTTCCTTCAT | GATCATCACA | ATCATCATCA | TTCTCATTCT | CATTTTTAA  ATCAACGAGT | 716 |
| ACTTCAAGAT | CTGAATTTGG | CTTGTTTGGA | GCATCTCCTC | TGCTCCCTG  GGGAGTCTGG | 776 |
| GCACAGTCAG | GTGGTGGCTT | AACAGGGAGC | TGGAAAAAGT | GTCCTTTCTT  CAGACACTGA | 836 |
| GGCTCCCGCA | GCAGCGCCCC | TCCCAAGAGG | AAGGCCTCTG | TGGCACTCAG  ATACCGACTG | 896 |
| GGGCTGGGGC | GCCGCCACTG | CCTTCACCTC | CTCTTTCAAA | CCTCAGTGAT  TGGCTCTGTG | 956 |
| GGCTCCATGT | AGAAGCCACT | ATTACTGGGA | CTGTCTCAGA | GACCCCTCTC  CCAGCTATTC | 1016 |
| CTACTCTCTC | CCCGACTCCG | AGAGCATGCT | TAATCTTGCT | TCTGCTTCTC  ATTTCTGTAG | 1076 |
| CCTGATCAGC | GCCGCACCAG | CCGGGAAGAG | GGTGATTGCT | GGGGCTCGTG  CCCTGCATCC | 1136 |
| CTCTCCTCCC | AGGGCCTGCC | CCACAGCTCG | GGCCCTCTGT | GAGATCCGTC  TTTGGCCTCC | 1196 |
| TCCAGAATGG | AGCTGGCCCT | CTCCTGGGGA | TGTGTAATGG | TCCCCCTGCT  TACCCGCAAA | 1256 |
| AGACAAGTCT | TTACAGAATC | AAATGCAATT | TTAAATCTGA | GAGCTCGCTT  GAGTGACTGG | 1316 |
| GTTTGTGATT | GCCTCTGAAG | CCTATGTATG | CCATGGAGGC | ACTAACAAAC  TCTGAGGTTT | 1376 |
| CCGAAATCAG | AAGCGAAAAA | ATCAGTGAAT | AAACCATCAT | CTTGCCACTA  CCCCCTCCTG | 1436 |
| AAGCCACAGC | AGGGGTTCAG | GTTCCAATCA | GAACTGTTGG | CAAGGTGACA  TTTCCATGCA | 1496 |
| TAGATGCGAT | CCACAGAAGG | TCCTGGTGGT | ATTTGTAACT | TTTTGCAAGG  CATTTTTTA | 1556 |
| TATATATTTT | TGTGCACATT | TTTTTTACG | ATTCTTTAGA | AAACAAATGT  ATTTCAAAAT | 1616 |
| ATATTTATAG | TCGAACAAGT | CATATATATG | AATGAGAGCC | ATATGAATGT  CAGTAGTTTA | 1676 |
| TACTTCTCTA | TTATCTCAAA | CTACTGGCAA | TTTGTAAAGA | AATATATATG  ATATATAAAT | 1736 |
| GTGATTGCAG | CTTTTCAATG | TTAGCCACAG | TGTATTTTTT | CACTTGTACT  AAAATTGTAT | 1796 |
| CAAATGTGAC | ATTATATGCA | CTAGCAATAA | AATGCTAATT | GTTTCATGGT  AAAAAAAAAA | 1856 |

( 2 ) INFORMATION FOR SEQ ID NO:5:

( i ) SEQUENCE CHARACTERISTICS:
        ( A ) LENGTH: 93 amino acids
        ( B ) TYPE: amino acid
        ( D ) TOPOLOGY: linear ( i i ) MOLECULE TYPE: protein ( x i ) SEQUENCE DESCRIPTION: SEQ ID NO:5:

```
Met  Asn  Ala  Lys  Val  Val  Val  Leu  Val  Leu  Val  Leu  Thr  Ala  Leu
1                    5                   10                  15
Cys  Leu  Ser  Asp  Gly  Lys  Pro  Val  Ser  Leu  Ser  Tyr  Arg  Cys  Pro  Cys
               20                       25                       30
```

|  | Arg | Phe | Phe 35 | Glu | Ser | His | Val | Ala 40 | Arg | Ala | Asn | Val | Lys 45 | His | Leu | Lys |
|---|---|---|---|---|---|---|---|---|---|---|---|---|---|---|---|---|
|  | Ile | Leu 50 | Asn | Thr | Pro | Asn | Cys 55 | Ala | Leu | Gln | Ile | Val 60 | Ala | Arg | Leu | Lys |
|  | Asn 65 | Asn | Asn | Arg | Gln | Val 70 | Cys | Ile | Asp | Pro | Lys 75 | Leu | Lys | Trp | Ile | Gln 80 |
|  | Glu | Tyr | Leu | Glu | Lys 85 | Ala | Leu | Asn | Lys | Arg 90 | Phe | Lys | Met |  |  |  |

( 2 ) INFORMATION FOR SEQ ID NO:6:

( i ) SEQUENCE CHARACTERISTICS:
        ( A ) LENGTH: 279 base pairs
        ( B ) TYPE: nucleic acid
        ( C ) STRANDEDNESS: single
        ( D ) TOPOLOGY: linear ( i i ) MOLECULE TYPE: cDNA to mRNA ( x i ) SEQUENCE DESCRIPTION: SEQ ID NO:6:

| ATGAACGCCA | AGGTCGTGGT | CGTGCTGGTC | CTCGTGCTGA | CCGCGCTCTG | CCTCAGCGAC | 60 |
|---|---|---|---|---|---|---|
| GGGAAGCCCG | TCAGCCTGAG | CTACAGATGC | CCATGCCGAT | TCTTCGAAAG | CCATGTTGCC | 120 |
| AGAGCCAACG | TCAAGCATCT | CAAAATTCTC | AACACTCCAA | ACTGTGCCCT | TCAGATTGTA | 180 |
| GCCCGGCTGA | AGAACAACAA | CAGACAAGTG | TGCATTGACC | CGAAGCTAAA | GTGGATTCAG | 240 |
| GAGTACCTGG | AGAAAGCTTT | AAACAAGAGG | TTCAAGATG |  |  | 279 |

( 2 ) INFORMATION FOR SEQ ID NO:7:

( i ) SEQUENCE CHARACTERISTICS:
        ( A ) LENGTH: 3526 base pairs
        ( B ) TYPE: nucleic acid
        ( C ) STRANDEDNESS: single
        ( D ) TOPOLOGY: linear ( i i ) MOLECULE TYPE: cDNA to mRNA ( x i ) SEQUENCE DESCRIPTION: SEQ ID NO:7:

| TCTCCGTCAG | CCGCATTGCC | CGCTCGGCGT | CCGGCCCCCG | ACCCGTGCTC | GTCCGCCCGC | 60 |
|---|---|---|---|---|---|---|
| CCGCCCGCCC | GCCCGCGCCA | TGAACGCCAA | GGTCGTGGTC | GTGCTGGTCC | TCGTGCTGAC | 120 |
| CGCGCTCTGC | CTCAGCGACG | GGAAGCCCGT | CAGCCTGAGC | TACAGATGCC | CATGCCGATT | 180 |
| CTTCGAAAGC | CATGTTGCCA | GAGCCAACGT | CAAGCATCTC | AAAATTCTCA | ACACTCCAAA | 240 |
| CTGTGCCCTT | CAGATTGTAG | CCCGGCTGAA | GAACAACAAC | AGACAAGTGT | GCATTGACCC | 300 |
| GAAGCTAAAG | TGGATTCAGG | AGTACCTGGA | GAAAGCTTTA | AACAAGAGGT | TCAAGATGTG | 360 |
| AGAGGGTCAG | ACGCCTGAGG | AACCCTTACA | GTAGGAGCCC | AGCTCTGAAA | CCAGTGTTAG | 420 |
| GGAAGGGCCT | GCCACAGCCT | CCCCTGCCAG | GGCAGGGCCC | CAGGCATTGC | CAAGGGCTTT | 480 |
| GTTTTGCACA | CTTTGCCATA | TTTTCACCAT | TTGATTATGT | AGCAAATAC | ATGACATTTA | 540 |
| TTTTTCATTT | AGTTTGATTA | TTCAGTGTCA | CTGGCGACAC | GTAGCAGCTT | AGACTAAGGC | 600 |
| CATTATTGTA | CTTGCCTTAT | TAGAGTGTCT | TTCCACGGAG | CCACTCCTCT | GACTCAGGGC | 660 |
| TCCTGGGTTT | TGTATTCTCT | GAGCTGTGCA | GGTGGGAGA | CTGGGCTGAG | GGAGCCTGGC | 720 |
| CCCATGGTCA | GCCCTAGGGT | GGAGAGCCAC | CAAGAGGGAC | GCCTGGGGGT | GCCAGGACCA | 780 |
| GTCAACCTGG | GCAAAGCCTA | GTGAAGGCTT | CTCTCTGTGG | GATGGGATGG | TGGAGGGCCA | 840 |
| CATGGGAGGC | TCACCCCCTT | CTCCATCCAC | ATGGGAGCCG | GTCTGCCTC | TTCTGGGAGG | 900 |
| GCAGCAGGGC | TACCCTGAGC | TGAGGCAGCA | GTGTGAGGCC | AGGGCAGAGT | GAGACCCAGC | 960 |

| | | | | | | |
|---|---|---|---|---|---|---|
| CCTCATCCCG | AGCACCTCCA | CATCCTCCAC | GTTCTGCTCA | TCATTCTCTG | TCTCATCCAT | 1020 |
| CATCATGTGT | GTCCACGACT | GTCTCCATGG | CCCCGCAAAA | GGACTCTCAG | GACCAAAGCT | 1080 |
| TTCATGTAAA | CTGTGCACCA | AGCAGGAAAT | GAAATGTCT | TGTGTTACCT | GAAACACTG | 1140 |
| TGCACATCTG | TGTCTTGTGT | GGAATATTGT | CCATTGTCCA | ATCCTATGTT | TTTGTTCAAA | 1200 |
| GCCAGCGTCC | TCCTCTGTGA | CCAATGTCTT | GATGCATGCA | CTGTTCCCCC | TGTGCAGCCG | 1260 |
| CTGAGCGAGG | AGATGCTCCT | TGGGCCCTTT | GAGTGCAGTC | CTGATCAGAG | CCGTGGTCCT | 1320 |
| TTGGGGTGAA | CTACCTTGGT | TCCCCCACTG | ATCACAAAAA | CATGGTGGGT | CCATGGGCAG | 1380 |
| AGCCCAAGGG | AATTCGGTGT | GCACCAGGGT | TGACCCCAGA | GGATTGCTGC | CCCATCAGTG | 1440 |
| CTCCCTCACA | TGTCAGTACC | TTCAAACTAG | GGCCAAGCCC | AGCACTGCTT | GAGGAAAACA | 1500 |
| AGCATTCACA | ACTTGTTTTT | GGTTTTAAA | ACCCAGTCCA | CAAAATAACC | AATCCTGGAC | 1560 |
| ATGAAGATTC | TTTCCCAATT | CACATCTAAC | CTCATCTTCT | TCACCATTTG | GCAATGCCAT | 1620 |
| CATCTCCTGC | CTTCCTCCTG | GGCCCTCTCT | GCTCTGCGTG | TCACCTGTGC | TTCGGGCCCT | 1680 |
| TCCCACAGGA | CATTTCTCTA | AGAGAACAAT | GTGCTATGTG | AAGAGTAAGT | CAACCTGCCT | 1740 |
| GACATTTGGA | GTGTTCCCCT | CCCACTGAGG | GCAGTCGATA | GAGCTGTATT | AAGCCACTTA | 1800 |
| AAATGTTCAC | TTTTGACAAA | GGCAAGCACT | TGTGGGTTTT | TGTTTTGTTT | TTCATTCAGT | 1860 |
| CTTACGAATA | CTTTTGCCCT | TTGATTAAAG | ACTCCAGTTA | AAAAAATTT | TAATGAAGAA | 1920 |
| AGTGGAAAAC | AAGGAAGTCA | AGCAAGGAA | ACTATGTAAC | ATGTAGGAAG | TAGGAAGTAA | 1980 |
| ATTATAGTGA | TGTAATCTTG | AATTGTAACT | GTTCGTGAAT | TTAATAATCT | GTAGGGTAAT | 2040 |
| TAGTAACATG | TGTTAAGTAT | TTTCATAAGT | ATTTCAAATT | GGAGCTTCAT | GGCAGAAGGC | 2100 |
| AAACCCATCA | ACAAAATTG | TCCCTTAAAC | AAAATTAAA | ATCCTCAATC | CAGCTATGTT | 2160 |
| ATATTGAAAA | AATAGAGCCT | GAGGGATCTT | TACTAGTTAT | AAAGATACAG | AACTCTTTCA | 2220 |
| AAACCTTTTG | AAATTAACCT | CTCACTATAC | CAGTATAATT | GAGTTTCAG | TGGGGCAGTC | 2280 |
| ATTATCCAGG | TAATCCAAGA | TATTTAAAA | TCTGTCACGT | AGAACTTGGA | TGTACCTGCC | 2340 |
| CCCAATCCAT | GAACCAAGAC | CATTGAATTC | TTGGTTGAGG | AAACAAACAT | GACCCTAAAT | 2400 |
| CTTGACTACA | GTCAGGAAAG | GAATCATTTC | TATTTCTCCT | CCATGGGAGA | AAATAGATAA | 2460 |
| GAGTAGAAAC | TGCAGGGAAA | ATTATTTGCA | TAACAATTCC | TCTACTAACA | ATCAGCTCCT | 2520 |
| TCCTGGAGAC | TGCCCAGCTA | AAGCAATATG | CATTTAAATA | CAGTCTTCCA | TTTGCAAGGG | 2580 |
| AAAAGTCTCT | TGTAATCCGA | ATCTCTTTTT | GCTTTCGAAC | TGCTAGTCAA | GTGCGTCCAC | 2640 |
| GAGCTGTTTA | CTAGGGATCC | CTCATCTGTC | CCTCCGGGAC | CTGGTGCTGC | CTCTACCTGA | 2700 |
| CACTCCCTTG | GGCTCCCTGT | AACCTCTTCA | GAGGCCCTCG | CTGCCAGCTC | TGTATCAGGA | 2760 |
| CCCAGAGGAA | GGGGCCAGAG | GCTCGTTGAC | TGGCTGTGTG | TTGGGATTGA | GTCTGTGCCA | 2820 |
| CGTGTATGTG | CTGTGGTGTG | TCCCCCTCTG | TCCAGGCACT | GAGATACCAG | CGAGGAGGCT | 2880 |
| CCAGAGGGCA | CTCTGCTTGT | TATTAGAGAT | TACCTCCTGA | GAAAAAGCT | TCCGCTTGGA | 2940 |
| GCAGAGGGGC | TGAATAGCAG | AAGGTTGCAC | CTCCCCAAC | CTTAGATGTT | CTAAGTCTTT | 3000 |
| CCATTGGATC | TCATTGGACC | CTTCCATGGT | GTGATCGTCT | GACTGGTGTT | ATCACCGTGG | 3060 |
| GCTCCCTGAC | TGGGAGTTGA | TCGCCTTTCC | CAGGTGCTAC | ACCCTTTTCC | AGCTGGATGA | 3120 |
| GAATTTGAGT | GCTCTGATCC | CTCTACAGAG | CTTCCCTGAC | TCATTCTGAA | GGAGCCCAT | 3180 |
| TCCTGGGAAA | TATTCCCTAG | AAACTTCCAA | ATCCCCTAAG | CAGACCACTG | ATAAAACCAT | 3240 |
| GTAGAAAATT | TGTTATTTTG | CAACCTCGCT | GGACTCTCAG | TCTCTGAGCA | GTGAATGATT | 3300 |
| CAGTGTTAAA | TGTGATGAAT | ACTGTATTTT | GTATTGTTTC | AAGTGCATCT | CCCAGATAAT | 3360 |

-continued

| GTGAAAATGG | TCCAGGAGAA | GGCCAATTCC | TATACGCAGC | GTGCTTTAAA | AAATAAATAA | 3420 |
| GAAACAACTC | TTTGAGAAAC | AACAATTTCT | ACTTTGAAGT | CATACCAATG | AAAAAATGTA | 3480 |
| TATGCACTTA | TAATTTTCCT | AATAAAGTTC | TGTACTCAAA | TGTAAA | | 3526 |

( 2 ) INFORMATION FOR SEQ ID NO:8:

( i ) SEQUENCE CHARACTERISTICS:
        ( A ) LENGTH: 3526 base pairs
        ( B ) TYPE: nucleic acid
        ( C ) STRANDEDNESS: single
        ( D ) TOPOLOGY: linear ( i i ) MOLECULE TYPE: cDNA to mRNA ( v i ) ORIGINAL SOURCE:
        ( A ) ORGANISM: Homo sapiens
        ( H ) CELL LINE: FLEB14

( i x ) FEATURE:
        ( A ) NAME/KEY: CDS
        ( B ) LOCATION: 80..361
        ( C ) IDENTIFICATION METHOD: by similarity to some other pattern ( i x ) FEATURE:
        ( A ) NAME/KEY: sig_peptide
        ( B ) LOCATION: 80..142
        ( C ) IDENTIFICATION METHOD: by similarity with known sequence
                or to an established consensus ( i x ) FEATURE:
        ( A ) NAME/KEY: mat_peptide
        ( B ) LOCATION: 143..358
        ( C ) IDENTIFICATION METHOD: by similarity with known sequence
                or to an established consensus ( x i ) SEQUENCE DESCRIPTION: SEQ ID NO:8:

| TCTCCGTCAG | CCGCATTGCC | CGCTCGGCGT | CCGGCCCCCG | ACCCGTGCTC | GTCCGCCCGC | 60 |

| CCGCCCGCCC | GCCCGCGCC | ATG | AAC | GCC | AAG | GTC | GTG | GTC | GTG | CTG | GTC | CTC | 112 |
| | | Met | Asn | Ala | Lys | Val | Val | Val | Val | Leu | Val | Leu | |
| | | -21 | -20 | | | | -15 | | | | | | |

| GTG | CTG | ACC | GCG | CTC | TGC | CTC | AGC | GAC | GGG | AAG | CCC | GTC | AGC | CTG | AGC | 160 |
| Val | Leu | Thr | Ala | Leu | Cys | Leu | Ser | Asp | Gly | Lys | Pro | Val | Ser | Leu | Ser | |
| -10 | | | | -5 | | | | | 1 | | | | 5 | | | |

| TAC | AGA | TGC | CCA | TGC | CGA | TTC | TTC | GAA | AGC | CAT | GTT | GCC | AGA | GCC | AAC | 208 |
| Tyr | Arg | Cys | Pro | Cys | Arg | Phe | Phe | Glu | Ser | His | Val | Ala | Arg | Ala | Asn | |
| | | 10 | | | | | 15 | | | | | 20 | | | | |

| GTC | AAG | CAT | CTC | AAA | ATT | CTC | AAC | ACT | CCA | AAC | TGT | GCC | CTT | CAG | ATT | 256 |
| Val | Lys | His | Leu | Lys | Ile | Leu | Asn | Thr | Pro | Asn | Cys | Ala | Leu | Gln | Ile | |
| | | 25 | | | | | 30 | | | | | 35 | | | | |

| GTA | GCC | CGG | CTG | AAG | AAC | AAC | AAC | AGA | CAA | GTG | TGC | ATT | GAC | CCG | AAG | 304 |
| Val | Ala | Arg | Leu | Lys | Asn | Asn | Asn | Arg | Gln | Val | Cys | Ile | Asp | Pro | Lys | |
| | 40 | | | | | 45 | | | | | 50 | | | | | |

| CTA | AAG | TGG | ATT | CAG | GAG | TAC | CTG | GAG | AAA | GCT | TTA | AAC | AAG | AGG | TTC | 352 |
| Leu | Lys | Trp | Ile | Gln | Glu | Tyr | Leu | Glu | Lys | Ala | Leu | Asn | Lys | Arg | Phe | |
| 55 | | | | | 60 | | | | | 65 | | | | | 70 | |

| AAG | ATG | TGAGAGGGTC | AGACGCCTGA | GGAACCCTTA | CAGTAGGAGC | CAGCTCTGA | 408 |
| Lys | Met | | | | | | |
| AACCAGTGTT | AGGGAAGGGC | CTGCCACAGC | CTCCCTGCC | AGGGCAGGGC | CCCAGGCATT | | 468 |
| GCCAAGGGCT | TTGTTTTGCA | CACTTTGCCA | TATTTTCACC | ATTTGATTAT | GTAGCAAAAT | | 528 |
| ACATGACATT | TATTTTTCAT | TTAGTTTGAT | TATTCAGTGT | CACTGGCGAC | ACGTAGCAGC | | 588 |
| TTAGACTAAG | GCCATTATTG | TACTTGCCTT | ATTAGAGTGT | CTTTCCACGG | AGCCACTCCT | | 648 |
| CTGACTCAGG | GCTCCTGGGT | TTTGTATTCT | CTGAGCTGTG | CAGGTGGGGA | GACTGGGCTG | | 708 |
| AGGGAGCCTG | GCCCCATGGT | CAGCCCTAGG | GTGGAGAGCC | ACCAAGAGGG | ACGCCTGGGG | | 768 |

| | | | | | |
|---|---|---|---|---|---|
| GTGCCAGGAC | CAGTCAACCT | GGGCAAAGCC | TAGTGAAGGC | TTCTCTCTGT | GGGATGGGAT | 828 |
| GGTGGAGGGC | CACATGGGAG | GCTCACCCCC | TTCTCCATCC | ACATGGGAGC | CGGGTCTGCC | 888 |
| TCTTCTGGGA | GGGCAGCAGG | GCTACCCTGA | GCTGAGGCAG | CAGTGTGAGG | CCAGGGCAGA | 948 |
| GTGAGACCCA | GCCCTCATCC | CGAGCACCTC | CACATCCTCC | ACGTTCTGCT | CATCATTCTC | 1008 |
| TGTCTCATCC | ATCATCATGT | GTGTCCACGA | CTGTCTCCAT | GGCCCCGCAA | AAGGACTCTC | 1068 |
| AGGACCAAAG | CTTTCATGTA | AACTGTGCAC | CAAGCAGGAA | ATGAAATGT | CTTGTGTTAC | 1128 |
| CTGAAAACAC | TGTGCACATC | TGTGTCTTGT | GTGGAATATT | GTCCATTGTC | CAATCCTATG | 1188 |
| TTTTTGTTCA | AAGCCAGCGT | CCTCCTCTGT | GACCAATGTC | TTGATGCATG | CACTGTTCCC | 1248 |
| CCTGTGCAGC | CGCTGAGCGA | GGAGATGCTC | CTTGGGCCCT | TGAGTGCAG | TCCTGATCAG | 1308 |
| AGCCGTGGTC | CTTTGGGGTG | AACTACCTTG | GTTCCCCCAC | TGATCACAAA | AACATGGTGG | 1368 |
| GTCCATGGGC | AGAGCCCAAG | GGAATTCGGT | GTGCACCAGG | GTTGACCCCA | GAGGATTGCT | 1428 |
| GCCCCATCAG | TGCTCCCTCA | CATGTCAGTA | CCTTCAAACT | AGGGCCAAGC | CCAGCACTGC | 1488 |
| TTGAGGAAAA | CAAGCATTCA | CAACTTGTTT | TTGGTTTTTA | AAACCCAGTC | CACAAATAA | 1548 |
| CCAATCCTGG | ACATGAAGAT | TCTTTCCAA | TTCACATCTA | ACCTCATCTT | CTTCACCATT | 1608 |
| TGGCAATGCC | ATCATCTCCT | GCCTTCCTCC | TGGGCCCTCT | CTGCTCTGCG | TGTCACCTGT | 1668 |
| GCTTCGGGCC | CTTCCCACAG | GACATTTCTC | TAAGAGAACA | ATGTGCTATG | TGAAGAGTAA | 1728 |
| GTCAACCTGC | CTGACATTTG | GAGTGTTCCC | CTCCCACTGA | GGGCAGTCGA | TAGAGCTGTA | 1788 |
| TTAAGCCACT | TAAAATGTTC | ACTTTGACA | AAGGCAAGCA | CTTGTGGGTT | TTTGTTTTGT | 1848 |
| TTTTCATTCA | GTCTTACGAA | TACTTTTGCC | CTTTGATTAA | AGACTCCAGT | TAAAAAAAT | 1908 |
| TTTAATGAAG | AAAGTGGAAA | ACAAGGAAGT | CAAAGCAAGG | AAACTATGTA | ACATGTAGGA | 1968 |
| AGTAGGAAGT | AAATTATAGT | GATGTAATCT | TGAATTGTAA | CTGTTCGTGA | ATTTAATAAT | 2028 |
| CTGTAGGGTA | ATTAGTAACA | TGTGTTAAGT | ATTTTCATAA | GTATTTCAAA | TTGGAGCTTC | 2088 |
| ATGGCAGAAG | GCAAACCCAT | CAACAAAAAT | TGTCCCTTAA | ACAAAAATTA | AAATCCTCAA | 2148 |
| TCCAGCTATG | TTATATTGAA | AAAATAGAGC | CTGAGGGATC | TTTACTAGTT | ATAAAGATAC | 2208 |
| AGAACTCTTT | CAAAACCTTT | TGAAATTAAC | CTCTCACTAT | ACCAGTATAA | TTGAGTTTTC | 2268 |
| AGTGGGGCAG | TCATTATCCA | GGTAATCCAA | GATATTTTAA | AATCTGTCAC | GTAGAACTTG | 2328 |
| GATGTACCTG | CCCCCAATCC | ATGAACCAAG | ACCATTGAAT | TCTTGGTTGA | GGAAACAAAC | 2388 |
| ATGACCCTAA | ATCTTGACTA | CAGTCAGGAA | AGGAATCATT | TCTATTTCTC | CTCCATGGGA | 2448 |
| GAAAATAGAT | AAGAGTAGAA | ACTGCAGGGA | AAATTATTTG | CATAACAATT | CCTCTACTAA | 2508 |
| CAATCAGCTC | CTTCCTGGAG | ACTGCCCAGC | TAAAGCAATA | TGCATTTAAA | TACAGTCTTC | 2568 |
| CATTTGCAAG | GGAAAAGTCT | CTTGTAATCC | GAATCTCTTT | TTGCTTTCGA | ACTGCTAGTC | 2628 |
| AAGTGCGTCC | ACGAGCTGTT | TACTAGGGAT | CCCTCATCTG | TCCCTCCGGG | ACCTGGTGCT | 2688 |
| GCCTCTACCT | GACACTCCCT | TGGGCTCCCT | GTAACCTCTT | CAGAGGCCCT | CGCTGCCAGC | 2748 |
| TCTGTATCAG | GACCCAGAGG | AAGGGGCCAG | AGGCTCGTTG | ACTGGCTGTG | TGTTGGGATT | 2808 |
| GAGTCTGTGC | CACGTGTATG | TGCTGTGGTG | TGTCCCCTC | TGTCCAGGCA | CTGAGATACC | 2868 |
| AGCGAGGAGG | CTCCAGAGGG | CACTCTGCTT | GTTATTAGAG | ATTACCTCCT | GAGAAAAAAG | 2928 |
| CTTCCGCTTG | GAGCAGAGGG | GCTGAATAGC | AGAAGGTTGC | ACCTCCCCA | ACCTTAGATG | 2988 |
| TTCTAAGTCT | TTCCATTGGA | TCTCATTGGA | CCCTTCCATG | GTGTGATCGT | CTGACTGGTG | 3048 |
| TTATCACCGT | GGGCTCCCTG | ACTGGGAGTT | GATCGCCTTT | CCAGGTGCT | ACACCCTTTT | 3108 |
| CCAGCTGGAT | GAGAATTTGA | GTGCTCTGAT | CCCTCTACAG | AGCTTCCCTG | ACTCATTCTG | 3168 |

|  |  |  |  |  | |
|---|---|---|---|---|---|
| AAGGAGCCCC | ATTCCTGGGA | AATATTCCCT | AGAAACTTCC | AAATCCCCTA | AGCAGACCAC | 3228 |
| TGATAAAACC | ATGTAGAAAA | TTTGTTATTT | TGCAACCTCG | CTGGACTCTC | AGTCTCTGAG | 3288 |
| CAGTGAATGA | TTCAGTGTTA | AATGTGATGA | ATACTGTATT | TTGTATTGTT | TCAAGTGCAT | 3348 |
| CTCCCAGATA | ATGTGAAAAT | GGTCCAGGAG | AAGGCCAATT | CCTATACGCA | GCGTGCTTTA | 3408 |
| AAAAATAAAT | AAGAACAAC | TCTTTGAGAA | ACAACAATTT | CTACTTTGAA | GTCATACCAA | 3468 |
| TGAAAAAATG | TATATGCACT | TATAATTTTC | CTAATAAAGT | TCTGTACTCA | AATGTAAA | 3526 |

( 2 ) INFORMATION FOR SEQ ID NO:9:

( i ) SEQUENCE CHARACTERISTICS:
        ( A ) LENGTH: 1797 base pairs
        ( B ) TYPE: nucleic acid
        ( C ) STRANDEDNESS: single
        ( D ) TOPOLOGY: linear ( i i ) MOLECULE TYPE: cDNA to mRNA ( x i ) SEQUENCE DESCRIPTION: SEQ ID NO:9:

|  |  |  |  |  | |
|---|---|---|---|---|---|
| GACCACTTTC | CCTCTCGGTC | CACCTCGGTG | TCCTCTTGCT | GTCCAGCTCT | GCAGCCTCCG | 60 |
| GCGCGCCCTC | CCGCCCACGC | CATGGACGCC | AAGGTCGTCG | CCGTGCTGGC | CCTGGTGCTG | 120 |
| GCCGCGCTCT | GCATCAGTGA | CGGTAAACCA | GTCAGCCTGA | GCTACCGATG | CCCCTGCCGG | 180 |
| TTCTTCGAGA | GCCACATCGC | CAGAGCCAAC | GTCAAGCATC | TGAAAATCCT | CAACACTCCA | 240 |
| AACTGTGCCC | TTCAGATTGT | TGCACGGCTG | AAGAACAACA | ACAGACAAGT | GTGCATTGAC | 300 |
| CCGAAATTAA | AGTGGATCCA | AGAGTACCTG | GAGAAAGCTT | TAAACAAGTA | AGCACAACAG | 360 |
| CCCAAGGAC | TTTCCAGTAG | ACCCCGAGG | AAGGCTGACA | TCCGTGGGAG | ATGCAAGGGC | 420 |
| AGTGGTGGGG | AGGAGGGCCT | GAACCCTGGC | CAGGATGGCC | GGCGGGACAG | CACTGACTGG | 480 |
| GGTCATGCTA | AGGTTTGCCA | GCATAAAGAC | ACTCCGCCAT | AGCATATGGT | ACGATATTGC | 540 |
| AGCTTATATT | CATCCCTGCC | CTCGCCCGTG | CACAATGGAG | CTTTTATAAC | TGGGGTTTTT | 600 |
| CTAAGGAATT | GTATTACCCT | AACCAGTTAG | CTTCATCCCC | ATTCTCCTCA | TCCTCATCTT | 660 |
| CATTTTAAAA | AGCAGTGATT | ACTTCAAGGG | CTGTATTCAG | TTTGCTTTGG | AGCTTCTCTT | 720 |
| TGCCCTGGGG | CCTCTGGGCA | CAGTTATAGA | CGGTGGCTTT | GCAGGGAGCC | CTAGAGAGAA | 780 |
| ACCTTCCACC | AGAGCAGAGT | CCGAGGAACG | CTGCAGGGCT | TGTCCTGCAG | GGGCGCTCC | 840 |
| TCGACAGATG | CCTTGTCCTG | AGTCAACACA | AGATCCGGCA | GAGGGAGGCT | CCTTTATCCA | 900 |
| GTTCAGTGCC | AGGGTCGGGA | AGCTTCCTTT | AGAAGTGATC | CCTGAAGCTG | TGCTCAGAGA | 960 |
| CCCTTTCCTA | GCCGTTCCTG | CTCTCTGCTT | GCCTCCAAAC | GCATGCTTCA | TCTGACTTCC | 1020 |
| GCTTCTCACC | TCTGTAGCCT | GACGGACCAA | TGCTGCAATG | GAAGGGAGGA | GAGTGATGTG | 1080 |
| GGGTGCCCCC | TCCCTCTCTT | CCCTTTGCTT | TCCTCTCACT | TGGGCCCTTT | GTGAGATTTT | 1140 |
| TCTTTGGCCT | CCTGTAGAAT | GGAGCCAGAC | CATCCTGGAT | AATGTGAGAA | CATGCCTAGA | 1200 |
| TTTACCCACA | AAACACAAGT | CTGAGAATTA | ATCATAAACG | GAAGTTTAAA | TGAGGATTTG | 1260 |
| GACCTTGGTA | ATTGTCCCTG | AGTCCTATAT | ATTTCAACAG | TGGCTCTATG | GGCTCTGATC | 1320 |
| GAATATCAGT | GATGAAAATA | ATAATAATAA | TAATAATAAC | GAATAAGCCA | GAATCTTGCC | 1380 |
| ATGAAGCCAC | AGTGGGGATT | CTGGGTTCCA | ATCAGAAATG | GAGACAAGAT | AAAACTTGCA | 1440 |
| TACATTCTTA | TGATCACAGA | CGGCCCTGGT | GGTTTTGGT | AACTATTTAC | AAGGCATTTT | 1500 |
| TTTACATATA | TTTTGTGCA | CTTTTTATGT | TTCTTTGGAA | GACAAATGTA | TTTCAGAATA | 1560 |
| TATTTGTAGT | CAATTCATAT | ATTTGAAGTG | GAGCCATAGT | AATGCCAGTA | GATATCTCTA | 1620 |
| TGATCTTGAG | CTACTGGCAA | CTTGTAAAGA | AATATATATG | ACATATAAAT | GTATTGTAGC | 1680 |

TTTCCGGTGT CAGCCACGGT GTATTTTCC ACTTGGAATG AAATTGTATC AACTGTGACA    1740

TTATATGCAC TAGCAATAAA ATGCTAATTG TTTCATGCTG TAAAAAAAAA AAAAAA    1797

( 2 ) INFORMATION FOR SEQ ID NO:10:

( i ) SEQUENCE CHARACTERISTICS:
        ( A ) LENGTH: 14 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:10:

AATTCGCGGC CGCT    14

( 2 ) INFORMATION FOR SEQ ID NO:11:

( i ) SEQUENCE CHARACTERISTICS:
        ( A ) LENGTH: 10 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: misc_feature
        ( B ) LOCATION: 1
        ( D ) OTHER INFORMATION: /label=phosphorylated ( x i ) SEQUENCE DESCRIPTION: SEQ ID NO:11:

AGCGGCCGCG    10

( 2 ) INFORMATION FOR SEQ ID NO:12:

( i ) SEQUENCE CHARACTERISTICS:
        ( A ) LENGTH: 28 base pairs
        ( B ) TYPE: nucleic acid
        ( C ) STRANDEDNESS: double
        ( D ) TOPOLOGY: linear ( i i ) MOLECULE TYPE: DNA (synthetic)

( x i ) SEQUENCE DESCRIPTION: SEQ ID NO:12:

GTAATACGAC TCACTATAGG GGAGAGCT    28

( 2 ) INFORMATION FOR SEQ ID NO:13:

( i ) SEQUENCE CHARACTERISTICS:
        ( A ) LENGTH: 28 base pairs
        ( B ) TYPE: nucleic acid
        ( C ) STRANDEDNESS: double
        ( D ) TOPOLOGY: linear ( i i ) MOLECULE TYPE: DNA (synthetic)

( x i ) SEQUENCE DESCRIPTION: SEQ ID NO:13:

CTCCCCTATA GTGAGTCGTA TTACTGCA    28

( 2 ) INFORMATION FOR SEQ ID NO:14:

( i ) SEQUENCE CHARACTERISTICS:
        ( A ) LENGTH: 32 base pairs
        ( B ) TYPE: nucleic acid
        ( C ) STRANDEDNESS: double
        ( D ) TOPOLOGY: linear ( i i ) MOLECULE TYPE: DNA (synthetic)

( x i ) SEQUENCE DESCRIPTION: SEQ ID NO:14:

CTAGTCTATA GTGTCACCTA AATCGTGGGT AC 32

( 2 ) INFORMATION FOR SEQ ID NO:15:

( i ) SEQUENCE CHARACTERISTICS:
    ( A ) LENGTH: 23 base pairs
    ( B ) TYPE: nucleic acid
    ( C ) STRANDEDNESS: double
    ( D ) TOPOLOGY: linear ( i i ) MOLECULE TYPE: DNA (synthetic)

( x i ) SEQUENCE DESCRIPTION: SEQ ID NO:15:

CACGATTTAG GTGACACTAT AGA 23

( 2 ) INFORMATION FOR SEQ ID NO:16:

( i ) SEQUENCE CHARACTERISTICS:
    ( A ) LENGTH: 44 base pairs
    ( B ) TYPE: nucleic acid
    ( C ) STRANDEDNESS: single
    ( D ) TOPOLOGY: linear ( i i ) MOLECULE TYPE: DNA (synthetic)

( x i ) SEQUENCE DESCRIPTION: SEQ ID NO:16:

AATATAGTCG ACCACCATGA ACGCCAAGGT CGTGGTCGTG CTGG 44

( 2 ) INFORMATION FOR SEQ ID NO:17:

( i ) SEQUENCE CHARACTERISTICS:
    ( A ) LENGTH: 37 base pairs
    ( B ) TYPE: nucleic acid
    ( C ) STRANDEDNESS: single
    ( D ) TOPOLOGY: linear ( i i ) MOLECULE TYPE: DNA (synthetic)

( x i ) SEQUENCE DESCRIPTION: SEQ ID NO:17:

CGGCGGACTA GTTTACTTGT TTAAAGCTTT CTCCAGG 37

( 2 ) INFORMATION FOR SEQ ID NO:18:

( i ) SEQUENCE CHARACTERISTICS:
    ( A ) LENGTH: 55 base pairs
    ( B ) TYPE: nucleic acid
    ( C ) STRANDEDNESS: single
    ( D ) TOPOLOGY: linear ( i i ) MOLECULE TYPE: DNA (synthetic)

( x i ) SEQUENCE DESCRIPTION: SEQ ID NO:18:

GCCGCCACTA GTTAGTGGT GGTGGTGGTG GTGCTTGTTT AAAGCTTTCT CCAGG 55

( 2 ) INFORMATION FOR SEQ ID NO:19:

( i ) SEQUENCE CHARACTERISTICS:
    ( A ) LENGTH: 39 base pairs
    ( B ) TYPE: nucleic acid
    ( C ) STRANDEDNESS: single
    ( D ) TOPOLOGY: linear ( i i ) MOLECULE TYPE: DNA (synthetic)

( x i ) SEQUENCE DESCRIPTION: SEQ ID NO:19:

CGGCGGACTA GTTCACATCT TGAACCTCTT GTTTAAAGC 39

( 2 ) INFORMATION FOR SEQ ID NO:20:

( i ) SEQUENCE CHARACTERISTICS:
        ( A ) LENGTH: 57 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:20:

```
GCCGCCACTA GTTCAGTGGT GGTGGTGGTG GTGCATCTTG AACCTCTTGT TTAAAGC                57
```

HUMAN STROMAL DERIVED FACTOR 1α AND 1β, AND DNAS ENCODING THE SAME

FIELD OF THE INVENTION

The present invention is related to novel polypeptides produced by human pro-B cell line and DNAs encoding them.

PURPOSE OF THE INVENTION

The present invention is related to novel polypeptides produced by hematopoietic cells and DNAs encoding them. It is known that many kinds of growth and differentiation factors, such as interleukin (IL), are secreted from hematopoietic cells.

This fact suggests that factors having similar or novel functions might be secreted therefrom in addition to the known factors already found.

The present inventors have paid attention to this point and attempted to find novel factors (polypeptide) produced from hematopoietic cells. The present inventions were screened by cross hybridization using mouse SDF-1 (Stromal Derived Factor 1; described in Japanese Patent Application No. 5-22098) cDNA as a probe to obtain human SDF-1 (2 kinds, α and β) produced from human pro-B cells.

When polypeptides having sequences identical or highly homologous with that of the polypeptide of the present invention and the DNAs encoding them are searched for with a computer, none are found out. Thus, it has been proved that the following polypeptides of the present invention and the DNAs coding the same are novel:

(1) a polypeptide having an amino acid sequence shown in SEQ ID NO. 1, (2) a DNA encoding the polypeptide described above in (1), (3) a DNA having a nucleotide sequence shown in SEQ ID NO. 2, (4) a DNA having a nucleotide sequence shown in SEQ ID NO. 3

(5) a polypeptide having an amino acid sequence shown in SEQ ID NO. 5, (6) a DNA encoding the polypeptide described above in (5), (7) a DNA having a nucleotide sequence shown in SEQ ID NO. 6, and (8) a DNA having a nucleotide sequence shown in SEQ ID NO. 7.

The present invention is concerned with polypeptides having the amino acid sequence shown in SEQ ID. No. 1 or 5, in substantially purified form, a homologue thereof, or a fragment of the sequence or homologue of a fragment, and DNA encoding such a polypeptide. More particularly, the present invention is related to DNA having the nucleotide sequence shown in SEQ ID No. 2 or 3, and 6 or 7 and DNA having a fragment which is able to selectively hybridize to the nucleotide sequence shown in SEQ ID No. 2 or 3, and 6 or 7.

A polypeptide of Seq. ID No. 1 or 5 in substantially purified form will generally comprise the polypeptide in a preparation in which more than 90%, e.g. 95%, 98% or 99% of the polypeptide in the preparation is that of Seq. ID No. 1 or 5.

A polypeptide homologue of the Seq. ID No. 1 or 5 will be generally at least 70%, preferably at least 80 or 90% and more preferably at least 95% homologous to the polypeptide of Seq. ID No. 1 over a region of at least 20, preferably at least 30, for instance 40, 60 or 80 more, contiguous amino acids. Such polypeptide homologues will be referred to below as a polypeptide according to the invention.

Generally, fragments of Seq. ID No. 1 or 5, or their homologues, will be at least 10, preferably at least 15, for example 20, 25, 30, 40, 50 or 60, amino acids in length, and are also encompassed by the term "a polypeptide according to the invention" as used herein.

A DNA capable of selectively hybridizing to the DNA of Seq. ID No. 2 or 3, and 6 or 7 will be generally at least 70%, preferably at least 80 or 90% and more preferably at least 95%, homologous to the DNA of Seq. ID No. 2 or 3 over a region of at least 20, preferably at least 30, for instance 40, 60 or 100 or more, contiguous nucleotides. Such DNA will be encompassed by the term "DNA according to the invention".

Fragments of the DNA of Seq. ID No. 2 or 3, and 6 or 7 will be at least 15, preferably at least 20, for example 25, 30 or 40, nucleotides in length, and are also encompassed by the term "DNA according to the invention" as used herein.

A further embodiment of the invention provides replication and expression vectors comprising DNA according to the invention. The vectors may be, for example, plasmid, virus or phage vectors provided with an origin of replication, optionally a promoter for the expression of said DNA and optionally a regulator of the promoter. The vector may contain one or more selectable marker genes, for example, an anpicillin resistance gene. The vector may be used in vitro, for example in the production of RNA corresponding to the DNA, or used to transfect or transform a host cell.

A further embodiment of the invention provides host cells transformed or transfected with the vectors for the replication and expression of DNA according to the invention, including the DNA SEQ. ID No. 2 or 3, and 6 or 7 or the open reading frame thereof. The cells will be chosen to be compatible with the vector and may, for example, be bacterial, yeast, insect or mammalian cells.

A further embodiment of the invention provides a method of producing a polypeptide which comprises culturing host cells of the present invention under conditions effective to express a polypeptide of the invention. Preferably, in addition, such a method is carried out under conditions in which the polypeptide of the invention is expressed and then produced from the host cells.

DNA according to the invention may also be inserted into the vectors described above in an antisense orientation in order to prove the production of antisense RNA. Antisense RNA may also be produced by synthetic means. Such antisense RNA may be used to control the level of a polypeptide of the invention in a cell.

The invention also provides monoclonal or polyclonal antibodies to a polypeptide according to the invention. The invention further provides a process for the production of monoclonal or polyclonal antibodies to the polypeptides of the invention. Monoclonal antibodies may be prepared by conventional hybridoma technology using a polypeptide of the invention or a fragment thereof, as an immunogen. Polyclonal antibodies may also be prepared by conventional means which comprise inoculating a host animal, for example a rat or a rabbit, with a polypeptide of the invention and recovering immune serum.

The present invention also provides pharmaceutical compositions containing a polypeptide of the invention, or an antibody thereof, in association with a pharmaceutically acceptable diluent and/or carrier.

The polypeptide of the present invention includes polypeptides in which a part of their amino acid sequence is lacking (e.g., a polypeptide comprised of only the essential sequence for revealing a biological activity from an amino acid sequence shown in SEQ ID No. 1 or 5), polypeptides in which a part of their amino acid sequence is replaced by other amino acids (e.g., those replaced by an amino acid having a similar property), and polypeptides in which other amino acids are added or inserted into a part of their amino acid sequence, as well as those having the amino acid sequence shown in SEQ ID NO. 1 or 5.

As is well known, there are one to six codons that encoding one amino acid (for example, it is known that there is one kind of codon for Met, and six codon for leucine (Leu)). Accordingly, the nucleotide sequence of DNA can be changed in order to encode a polypeptide having the same amino acid sequence.

The DNA of the present invention, specified in (2) and (6), listed above, includes a group of every nucleotide sequence encoding polypeptides shown in SEQ ID NO. 1 and 5. There is a probability of improving the production yield of a polypeptide by changing a nucleotide sequence.

The DNAs specified in (3) and (7), listed above, are the embodiment of DNAs shown in (2) respectively and (6), and are the natural form of the sequence.

The DNAs shown in (4) and (8), listed above, indicate the sequence of the DNAs specified in (3) and (7), respectively with a untranslated region.

A signal peptide is a hydrophobic region located immediately downstream of the translation initiation amino acid Met. It is assumed that the signal peptide in the polypeptide of the present invention resides in a region ranging from Met, at the 1-position, to Gly at the 21-position, in the amino acid sequence represented by Seq. ID No. 1 or 5. The region essentially responsible for the expression of the biological activity corresponds to the part of the amino acid sequences of the Seq. ID. No. 1 and 5 that lack signal peptides, i.e. the mature protein part. Thus, signal peptides never relate to biological activity.

The DNA having a nucleotide sequence shown in SEQ ID NO. 3 or 7 may be prepared according to the following method:

(i) isolating mRNA from a cell which produces the polypeptide of the present invention (e.g., human pro-B cell line), (ii) preparing a first strand of cDNA (single strand cDNA) from mRNA obtained as (i) above, followed by preparing a second strand of cDNA (double strand cDNA) (synthesis of cDNA), (iii) inserting cDNA obtained as in (ii) above, into a proper phage vector, (iv) transfecting recombinant phage into host cells (construction of a cDNA library), (v) screening by plaque hybridization, a cDNA library using mouse SDF-1 cDNA as a probe, (vi) preparing phage DNA from a positive clone, followed by cutting out and subcloning the cDNA, and preparing the restriction enzyme map.

(vii) determining the nucleotide sequence of each fragment cut by restriction enzymes, followed by assembling the sequence of the full length sequence.

Explained in detail, step (i) may be carried out in accordance with the method of Okayama et al (described in Enzymology, vol. 154, p3, 1987) after a human pro-B cell line is stimulated by a proper stimulant (e.g. IL-1 etc.) or without stimulation.

An example of the cell which secretes the polypeptides of the present invention is preferably the human pro-B cell line FLEB14. Human cell line FLEB14 may be supplied by 1st lecture, Medicinal Chemistry, School of Medicine, Kyoto University.

Steps (ii), (iii) and (iv) are a series of steps for preparing a cDNA library, and may be carried out in accordance with the method of Glubler & Hoffman (Gene, vol. 25, pp. 263, 1983) with a slight modification.

As examples of the vector used in the step (iii), many plasmid vectors (e.g. pB322, pBluescript etc.), and phage vectors (e.g. λgt10, λDASH II etc.) are known, and phage vector λgt10 (43.3 kbp, Stratagene) is preferable.

The host cell used in step (iv) is preferably *E. coli* NM514 (Stratagene).

Steps (v) and (vi) may be carried out in accordance with the method described in Molecular Cloning (written by Sam Brook, Fritsh, E. F. and Maniatis, T., published by Cold Spring Harbor Laboratory Press in 1989.).

DNA sequencing according to step (vii) may be carried out in accordance with the method of Maxam-Gilbert or the dideoxy termination method.

It is necessary to confirm that the cDNA obtained covers a complete or almost complete length of intact mRNA. This confirmation may be carried out by Northern analysis using the cDNA as a probe (see Molecular Cloning).

If the size of the mRNA obtained from the hybridized band and the size of the cDNA are almost same, the cDNA is considered to be almost full length.

Once the nucleotide sequences shown in SEQ ID NOs. 2, 3, 6, 7 are determined, DNA of the present invention may be obtained by chemical synthesis, by the PCR method, or by the hybridization making use of a fragment of DNA of the present invention as a probe. Furthermore, DNA of the present invention may be obtained in a desired amount by transforming a DNA of the present invention into a proper host, with a vector that contains DNA according to the present invention followed by culturing the transformant.

The polypeptides of the present invention (shown in SEQ ID NO. 1 or 5) may be prepared by:

(1) isolating and purifying such polypeptides from an organism or a cultured cell, (2) chemical synthesis, or (3) using a skill of biotechnology, preferably, by the method described in (3).

Examples of the expression system that may be used when preparing a polypeptide by using a skill of biotechnology, are, for example, the expression systems of bacteria, yeast, insect cells and mammalian cells.

For example, the expression in *E. coli* may be carried out by adding the initiation codon (ATG) to 5' end of a DNA encoding the mature protein, connecting the DNA thus obtained downstream of a proper promoter (e.g., trp promoter, lac promoter, lPL promoter, and T7 promoter) and then inserting it into a vector (e.g., pBR322, pUC18, and pUC19) which functions in an *E. coli* strain, to prepare an expression vector.

When a bacterial signal peptide (e.g., signal peptide of pel B) is utilized, the desired polypeptide may also be produced in periplasm. Furthermore, a fusion protein with another polypeptide may also be easily produced.

Furthermore, expression in a mammalian cell may be carried out, for example, by inserting the DNA shown in SEQ ID NO. 3 or 6 downstream of a proper promoter (e.g., SV40 promoter, LTR promoter, and metallothionein promoter) in a proper vector (e.g., retrovirus vector, papilloma virus vector, vaccinia virus vector, and SV40 vector) to obtain an expression vector, and transfecting a proper mammalian cell (e.g., monkey COS-7 cell, Chinese hamster CHO cell, and mouse L cell) with the expression vector thus obtained, and then culturing the transformant in a proper medium to get the desired polypeptide in the culture medium. The polypeptide thus obtained may be isolated and purified by conventional biochemical methods.

EFFECTS OF THE INVENTION

Figure 1:
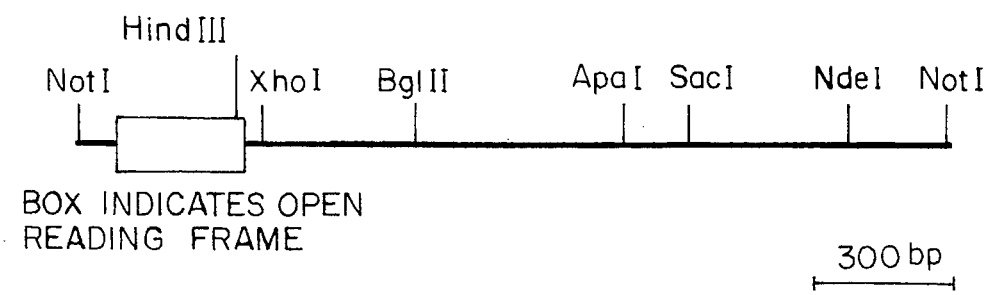
FIG. 1 is the restriction enzyme map of the cDNA clone (1.9 kb) of SDF-1α.

Polypeptides of the present invention are produced and secreted in pro-B cells, so they may be used for diseases relating to undergrown or abnormal proliferation of hematopoietic cells, neuronal enhancement or depression, immunological enhancement and depression; for example, inflammatory diseases (rheumatoid arthritis, ulcerative colitis), hematopoietic stemcytopenia after bone marrow transplantation, leukocytopenia, thrombocytopenia, B lymphopenia and T lymphopenia after chemotherapy, anemia, infectious diseases, cancer, leukocytosis, AIDS, neurodegenerative diseases (Alzheimer, multiple sclerosis), prevention or treatment of neuronal injury, prevention or treatment of disorders of bone metabolism (osteoporosis) or tissue repair.

In regard to the above activities, it was confirmed that mouse SDF-1α stimulated the proliferation of the mouse myeloid progenitor cell line DA1G in the laboratory test. It was suggested that human SDF-1α also has the same activity.

Further, polyclonal or monoclonal antibodies against the polypeptide of the present invention can be used in the determination of the amount of said polypeptide in the organism, and thereby, may be utilized for the purpose of investigating the relationship between the polypeptide and diseases, or for the purpose of diagnosing diseases. Polyclonal and monoclonal antibodies may be prepared by conventional methods by using the said polypeptide or the fragment thereof as an antigen.

The DNA of the present invention may be utilized as an important and essential template in preparing the polypeptide of the present invention, which is expected to for the diagnosis and treatment of genetic diseases (the treatment of gene defect diseases by inhibiting expression of the polypeptide by antisense DNA (RNA)). Further, genomic DNA may be isolated by using the DNA of the present invention as a probe. Similarly, it is possible to isolate genes having high homology to the DNA of the present invention in humans or other species.

Application as Pharmaceuticals

The polypeptides of the present invention are produced and secreted in pro-B cells, so they may be used for diseases relating to undergrown or abnormal proliferation of hematopoietic cells, neuronal enhancement or depression, immunological enhancement and depression; for example, inflammatory diseases (rheumatoid arthritis, ulcerative colitis), hematopoietic stemcytopenia after bone marrow transplantation, leukocytopenia, thrombocytopenia, B lymphopenia and T lymphopenia after chemotherapy, anemia, infectious diseases, cancer, leukocytosis, AIDS, neurodegenerative diseases (Alzheimer, multiple sclerosis), prevention or treatment of neuronal injury, prevention or treatment of disorders of bone metabolism (osteoporosis) or tissue repair.

The polypeptides of the present invention may be administered systemically or partially, usually by oral or parenteral administration; preferably by orally, intravenously or intraventricularly administration.

The doses to be administered are determined depending upon age, body weight, symptom, the desired therapeutic effect, the route of administration, and the duration of the treatment. In the human adult, doses per person per dose are generally between 100 μg and 100 mg; by oral administration, up to several times per day, and between 10 μg and 100 mg, by parenteral administration up to several times per day.

As mentioned above, the doses to be used depend upon various conditions. Therefore, there are cases in which doses lower than or greater than the ranges specified above may be used.

Administration of the compounds of the present invention; may be as solid compositions, liquid compositions or other compositions for oral administration; and as injections, liniments or suppositories for parenteral administration.

Solid compositions for oral administration include compressed tablets, pills, capsules, dispersible powders, and granules. Capsules include soft capsules and hard capsules.

In such compositions, one or more of the active compound(s) is or are admixed with at least one inert diluent (such as lactose, mannitol, glucose, hydroxypropyl cellulose, microcrystalline cellulose, starch, polyvinylpyrrolidone, or magnesium metasilicate aluminate). The compositions may also comprise additional substances other than inert diluents e.g. lubricating agents (such as magnesium stearate etc.), disintegrating agents (such as cellulose calcium glycolate, etc.), stabilizing agents (such as human serum albumin, lactose etc.), and assisting agents for dissolving (such as arginine, asparaginic acid).

The tablets or pills may, if desired, be coated with a film of gastric or enteric material (such as sugar, gelatin, hydroxypropyl cellulose or hydroxypropylmethyl cellulose phthalate), or be coated with more than two films. And further, the coating may be containment within capsules of absorbable materials, such as gelatin.

Other compositions for oral administration included spray compositions which may be prepared by known methods and which comprise one or more of the active compound(s). Spray compositions may comprise additional substances other than inert diluents, e.g. stabilizing agents (sodium sulfite), and isotonic buffers (sodium chloride, sodium citrate, citric acid). For preparation of such spray compositions, for example, the method described in the U.S. Pat. Nos. 2,868,691 or 3,095,355 (herein incorporated in their entireties by reference) may be used.

Injections may comprise additional substances other than inert diluents, e.g. preserving agents, wetting agents, emulsifying agents, dispersing agents, stabilizing agent (such as human serum albumin, lactose), and assisting agents such as assisting agents for dissolving (arginine, asparaginic acid).

These substances may be sterilized, for example, by filtration through a bacteria-retaining filter, by incorporation of sterilizing agents in the compositions or by irradiation. They may also be manufactured in the form of sterile solid compositions, for example, by freeze-drying, and which can be dissolved in sterile water or some other sterile diluents for injection immediately before used.

Other compositions for parenteral administration include liquids for external use, endermic liniments (ointment), suppositories for rectal administration and pessaries, which comprise one or more of the active compound(s) and may be prepared by known methods.

EXAMPLES

The following examples illustrate, but do not limit, the present invention.

Example 1: Northern Analysis of Human Cell Line FLEB14

Human pro-B cell line FLEB14 cells (See Katamine, S., et al. Nature, 309, 369 (1984)) were homogenated. The homogenate was incubated with oligo-dT cellulose. Poly(A) RNA was eluted after washing (Vennstorm, B. et al Cell, 28, 135(1982)). 1 μg of poly(A) RNA was electrophoresed in a 1.0% agarose gel and then blotted to a nitrocellulose membrane.

The membrane was hybridized with the 32P-labeled mouse SDF-1 (described as seq. ID No. 3 in Japanese Patent Application No.5-22098; the sequence is shown in seq. ID No. 9.; the factor is now called SDF-1α, as another SDF-1 was found from mouse) cDNA with 50% formamide, 5 X SSC, 0.1% SDC, 0.1% SDS, 5 X Denhaldt's, 0.1 mg/ml Salmon sperm DNA at 39° C. and washed with 0.3M NaCl, 30 mM Na citrate, 0.1% SDS at 50° C. and then autoradiogramed. 3.5 kb and 1.9 kb mRNA hybridized.

Example 2: Preparation of cDNA From mRNA of Human pro-B Cell Line

A cDNA library was constructed from human pro-B cell line FLEB14 cells by the conventional method (See Molecular Cloning; Sambrook, J., Fritsh, E. F., & Maniatis, T, Cold Spring Harbor Laboratory Press (1989)). cDNA was synthesized using Time Saver cDNA synthesis kit (Pharmacia).

The first strand was synthesized from FLEB14 poly(A)-RNA (5 μg) using a reverse transcriptase and an oligo-dT primer. The double strand cDNA was synthesized using DNA polymerase I.

cDNA was ligated with an EcoRI-NotI adapter:

AATTCGCGGCCGCT (SEQ ID NO. 10)
    GCGCCGGCGAp (SEQ ID NO. 11)

and then phosphorylated, cDNA larger than 800 bp were recovered from a 0.8% agarose gel with a glass powder (Geneclean II DNA purification kit, available from Bio101).

Example 3: Preparation of cDNA Library and Cross Hybridization

The cDNA obtained in Example 2 was ligated into a λgt10 phase vector (available from Stratagene) which have EcoRI arm treated with phosphatase.

In vitro packaging followed the protocol of the in vitro packaging kit LAMDA INN (available from Nihon gene). The recombinant phages were transfected to host *E. Coil* NM514 (available from Stratagene). A cDNA library containing 1×10 6 plaques was obtained. 1×10 6 λgt10 phage plaques of the cDNA library were transfected to nitrocellulose membranes. The membranes were hybridized with the 32P-labeled mouse SDF-1α cDNA (shown in seq. ID no.9, same cDNA used in Example 1)in 50% formamide, 5 X SSD, 0.1% SDS, 5 X Denhaldt's 0.1 mg/ml Salmon sperm DNA, at 39° C. and washed in 0.3 M NaCl, 30 mM Na citrate, 0.1% SDS at 50° C. and autoradiogramed. 40 positive clones were obtained.

Example 4: Isolation of Positive Clones

Phage DNA was prepared from 9 positive clones by the conventional method (See Cell Technology Experimental Protocol, pp. 8, published by Shuujun-sha). Phage DNA was digested with Not I. The length of inserted cDNA were measured by agarose gel electrophoresis. 8 clones were 1.9 kb long, the length of one clone was 3.5 kb long. It was thought that these two types of clones are almost full length human SDF-1α and SDF-β cDNA from the result of a Northern analysis.

cDNA from one clone 1.9 kb in length, and from one clone 3.5 kb in length was digested with Not I; subjected to agarose electrophoresis, and the fragments were cut out and then subcloned at the Not I site of plasmid pBluescript.

Example 5: Preparation of Restriction Enzyme Map and Sequencing

A restriction enzyme map of human SDF-1 (1.9 kb) was prepared (shown in FIG. 1). Nucleotide sequences of about 300 bp from both ends of each restriction fragment where determined. Upon assembling these sequences, the full length nucleotide sequences were determined (shown in Seq. ID. No. 3).

An open reading frame and an amino acid sequence were determined from the nucleotide sequence of the full length cDNA, with the results shown in Seq. ID No. 1. 30–40 amino acids of the N-termini obtained was compared with known signal peptides and a signal peptide of the polypeptides of the present invention was presumed (sequence shown in seq. ID No. 4) (See Von Heuane, G. Nucleic Acids Res. 14, 4683 (1986)).

Figure 2:
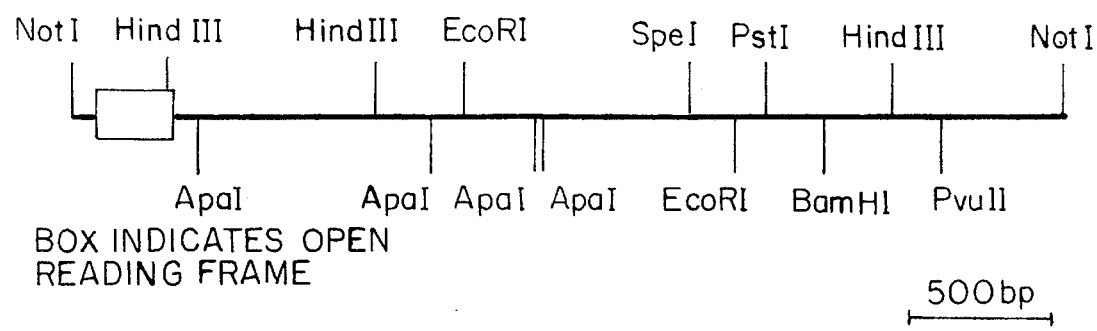
FIG. 2 is the restriction enzyme map of the cDNA clone (3.5 kb) of SDF-1β.

By the same procedure as described above, a restriction enzyme map (shown in FIG. 2), full length nucleotide sequences (shown in seq. ID No. 7), an open reading frame (shown in seq. ID No. 6), an amino acid sequence (shown in seq. ID No. 5) and a signal peptide sequence (shown in seq. ID No. 8) of the 3.5 kb clone were obtained.

The deduced amino acid sequences of the 3.5 kb clone and the 1.9 kb clone were very similar each other, so the 1.9 kb clone was named SDF-1α and the 3.5 kb clone was named SDF-1β.

The nucleotide sequences were determined by the cycle sequence method using a fluorescence determinator (supplied by Applied Biosystem Inc.). Nucleotide sequences were read by a DNA sequencer (Model 373, supplied by Applied Biosystem Inc.).

The nucleotide sequences and the deduced amino acid sequences of SDF-1α and 1β were homology searched in a computer data base (GENBANK and EMBL for DNA, NBRF and SWISSPROT for amino acid sequence). It was confirmed that cDNAs of the present invention encode novel peptides.

Example 6: Construction of Plasmid Vector for Use in the Preparation of an Expression Vector As an expression vector, a pUC-SRαML-1 (preparation of which is disclosed in European Patent publication No. 559428) derivative was used. This derivative was constructed so as to insert two fragments, as shown below:

fragment T7  5' GTAATACGACTCACTATAGGGGAGAGCT 3' (SEQ ID NO. 12)
             3' ACGTCATTATGCTGAGTGATATCCCCTC 5' (SEQ ID NO. 13)

between the PstI and SacI sites and fragment SP6  5' CTAGTCTATAGTGTCACCTAAATCGTGGGTAC 3' (SEQ ID NO. 14)
              3' AGATATCACAGTGGATTTAGCAC 5' (SEQ ID NO. 15)

between the SpeI and KpnI sites in the multi-cloning site, respectively.

Figure 3:
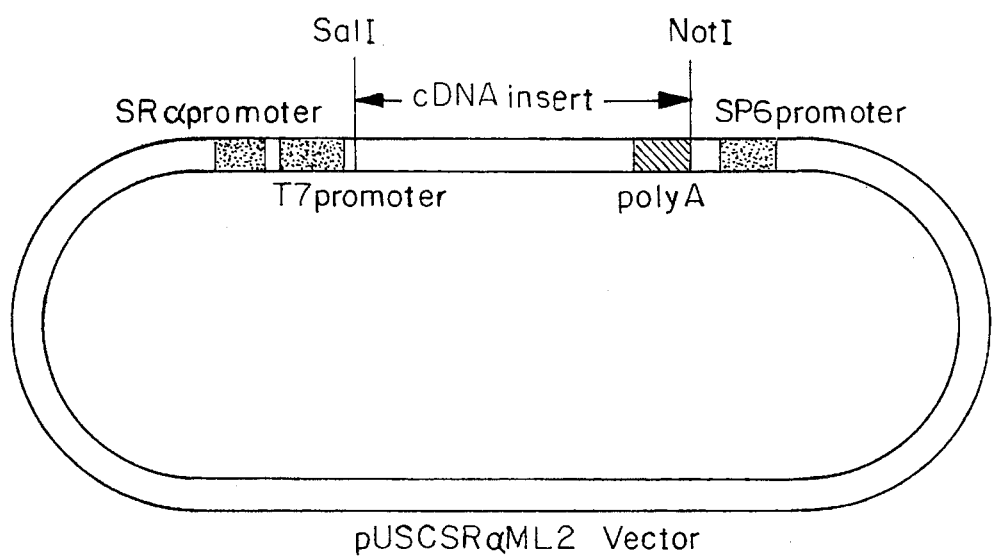
FIG. 3 is the map of the plasmid vector pUC-SR αML2.

The pUC-SRαML1 vector was digested with PstI and SacI and the resulting digest was subjected to agarose gel electrophoresis to prepare and recover about a 4.1 kbp fragment and thereafter the 5'-end phosphoric acid group was removed by BAP (bacterial alkaline phosphatase) treatment. The phosphorylated DNA fragment T7 was ligated with the thus prepared about 4.1 kbp fragment from pUC-SRαML1 to make a circular form. The resulting vector was, then, digested with SpeI and KpnI and the resulting digest was subjected to agarose gel electrophoresis to prepare and recover an about 4.1 kbp fragment and thereafter the 5'-end phosphoric acid group was removed by BAP (bacterial alkaline phosphatase) treatment. The phosphorylated DNA fragment SP6 was ligated with the thus prepared about 4.1 kbp fragment to make a circular form. The plasmid vector constructed in this manner was named pUC-SRαML2 (See FIG. 3).

Example 7: Construction of Expression Vector

Regarding hSDF-1α, primer X, Y and YH were synthesized. The sequence of primer X, Y and YH are as follows:

Primer X
5'- A   ATA TAG TCG ACC ACC ATG AAC GCC AAG GTC GTG GTC GTG CTG G-3' (SEQ ID NO. 16)

Primer Y
5'- CGG CGG ACT AGT TTA CTT GTT TAA AGC TTT CTC CAG G-3' (SEQ ID NO. 17)

Primer YH
5'- GCC GCC ACT AGT TTA GTG GTG GTG GTG GTG GTG CTT GTT TAA AGC TTT CTC CAG G-3' (SEQ ID NO. 18)

The hSDF-1α plasmid was subjected to PCR using the thus synthesized oligonucleotides X and Y as primers. The thus obtained PCR fragment contains a sequence placed 5'-adjacent to the initiation codon, that corresponds to the Kozac sequence which is known among those skilled in the art, and cDNA which encodes a protein molecule consisting of the hSDF-1α protein. The PCR fragment was digested with SalI and SpeI and the resulting digest was separated and purified and then inserted into the SalI— SpeI site of pUC-SRαML2 prepared in example 6, to obtain the expression vector pUC-SRαML2—hSDF-1αA.

Moreover, the hSDF-1α plasmid was subjected to PCR using the synthesized oligonucleotides X and YH as primers. The thus obtained PCR fragment contains a sequence placed 5'-adjacent to the initiation codon, that corresponds to Kozac sequence which is known among those skilled in the art, and cDNA which encodes a protein molecule consisting of the hSDF-1α protein and six additional histidine (His) residues attached to its C-terminal end. The PCR fragment was digested with SalI and SpeI and the resulting digest was separated and purified and then inserted into the SalI—SpeI site of pUC-SRαML2 prepared in example 6, to obtain the expression vector pUC-SRαML2—hSDF-1αB.

As for hSDF-1β, primer Z and ZH were synthesized. Sequences of primer Z and ZH are as follows:

Primer Z
5'- CGG CGG ACT AGT TCA CAT CTT GAA CCT CTT GTT TAA AGC-3' (SEQ ID NO. 19)

Primer ZH
5'- GCC GCC ACT AGT TCA GTG GTG GTG GTG GTG GTG CAT CTT GAA CCT CTT GTT TAA AGC-3' (SEQ ID NO. 20)

The hSDF-1β plasmid was subjected to PCR using the thus synthesized oligonucleotides X and Z as primers. The thus obtained PCR fragment contains a sequence placed 5'-adjacent to the initiation codon, that corresponds to the Kozac sequence which is known among those skilled in the art, and cDNA which encodes a protein molecule consisting of the hSDF-1β protein. The PCR fragment was digested with SalI and SpeI and the resulting digest was separated and purified and then inserted into the SalI—SpeI site of pUC-SRαML2 prepared in example 6 to obtain the expression vector pUC-SRαML2—hSDF-1βA.

Moreover, the hSDF-1β plasmid was subjected to PCR using the synthesized oligonucleotides X and ZH as primers. The thus obtained PCR fragment contains a sequence placed 5'-adjacent to the initiation codon, that corresponds to the Kozac sequence which is known among those skilled in the art, and cDNA which encodes a protein molecule consisting of the hSDF-1β protein and six additional histidine (His) residues attached to its C-terminal end. The PCR fragment was digested with SalI and SpeI and the resulting digest was separated and purified and then inserted into the SalI—SpeI site of the pUC-SRαML2 prepared in example 6, to obtain the expression vector pUC-SRαML2—hSDF-1βB.

Each of the thus constructed pUC-SRαML2-hSDF-1αA, pUC-SRαML2-hSDF-1αB, pUC-SRαML2-hSDF-1βA and pUC-SRαML2-hSDF-1β plasmids were transfected into E.

coli strain DH5, recovered from a 100 ml culture of the resulting transformant and then purified by CsCl density gradient centrifugation twice.

Example 8: Expression in COS Cells

Each of the plasmid DNA preparations pUC-SRαML2, pUC-SRαML2-hSDF-1αA, pUC-SRαML2-hSDF-1αB, pUC-SRαML2-hSDF-1βA and pUC-SRαML2-hSDF-1βB were introduced into COS-7 cells (Cell, vol. 23, p. 175, 1981) by means of the diethylaminoethyl (DEAE) dextran method (J. Immunology, vol. 136, p. 4291, 1986).

That is, about 1.8×10⁶ COS-7 cells were inoculated into a 225 cm² capacity flask (manufactured by Corning) together with 50 ml of a liquid culture medium (Dulbecco's modified MEM medium supplemented with 10% decomplemented fetal bovine serum). After overnight incubation in a carbon dioxide incubator (37° C., 5% CO2) and subsequent removal of the culture supernatant, 12 ml of a DNA cocktail (Dulbecco's modified MEM medium supplemented with 15 µg of each plasmid DNA, 50 mM Tris-HCl buffer (pH 7.4) and 400 µg/ml of DEAE-dextran) was added to each flask and culturing was carried out for 3 hours at 37° C. in an atmosphere of 5% CO2. Thereafter, the DNA cocktail was replaced by 15 ml of a chloroquine solution (Dulbecco's modified MEM medium supplemented with 150 µM chloroquine and 7% decomplemented fetal bovine serum), followed by additional 3 hours of culturing.

After removing the chloroquine solution, the aforementioned liquid culture medium (50 ml) was added to each of the resulting flasks which were then incubated at 37° C. in an atmosphere of 5% CO2 for 72 hours until growth of the cells in each flask almost forms a monolayer. After removing the culture supernatant, the cells in each flask were washed with a serum-free liquid culture medium (trade name, SFM-101; available from Nissui Pharmaceutical Co., Ltd.) and then supplied with 75 ml of the same serum-free liquid culture medium, and the culturing was continued for another 72 hours. Thereafter, the resulting culture supernatant was recovered and filtered through a membrane filter (trade name, STERIVEX-GS; available from Millipore Corp.) to remove the cells and cell debris. The thus obtained culture supernatant samples were stored at 4° C. for future use. A culture supernatant of COS cells which have been transformed with plasmid containing the hSDF-1α and β cDNA inserts are expected to contain expressed and secreted mature protein moieties of polypeptides which correspond to hSDF-1α and β.

Example 9: Confirmation of Expression

A 2 ml portion of each of the culture supernatants of transformed COS cells obtained in Example 8 was concentrated to a volume of 100 ml using a centrifugal concentration filter (trade name, Centricon-10; available from Millipore Corp.). A 1 µl portion of each of the thus concentrated samples was mixed with the same volume of a loading buffer (0.125M Tris-HCl buffer (pH 6.8), 4% sodium dodecyl sulfate and 30% glycerol) for SDS-PAGE (sodium dodecyl sulfate polyacrylamide gel electrophoresis) use, and the mixture was treated at 90° C. for 3 minutes and then subjected to SDS-PAGE.

In the case of the hSDF-1αB and βB proteins having the His hexamer introduced to the C-terminus of the proteins, not only their corresponding COS cell culture supernatant but also their purified products were subjected to SDS-PAGE analysis.

Purification of the protein was carried out by means of metal chelate affinity chromatography (Biotechnology, vol. 9, p. 273, 1991), making use of the function of His to form complex compounds with various transition metal ions. That is, a culture supernatant (350 ml) obtained from COS cells was mixed with a sodium chloride aqueous solution in such an amount that the final concentration of the salt became 1M, and the resulting mixture was applied to a column packed with 4 ml of a zinc-linked chelating Sepharose (trade name, Chelating Sepharose Fast-Flow; available from Pharmacia) to adsorb the protein to the resin. The column was washed with 50 mM phosphate buffer (pH 7.0) containing 1M sodium chloride aqueous solution (40 ml), and the protein retained in the column was eluted with 50 mM phosphate buffer (pH 7.0) containing 1M sodium chloride aqueous solution and 0.4M imidazole. Thereafter, the resulting elute was concentrated to a volume of 100 µl, and a portion of the concentrated sample was subjected to SDS-PAGE analysis. The SDS-PAGE analysis was carried out using a SDS 10/20 gradient gel and a product which corresponds to a molecular weight of hSDF-1α and SDF-1β was detected, respectively.

What is claimed is:

1. An isolated DNA molecule encoding a Stromal Derived Factor-1α (SDF-1α) polypeptide, having the amino acid sequence shown in SEQ ID NO:1.

2. An isolated DNA molecule comprising a DNA molecule having the nucleotide sequence shown in SEQ ID NO:2, or a nucleotide sequence complementary thereto.

3. An isolated DNA molecule comprising a DNA molecule having the nucleotide sequence shown in SEQ ID NO:3 or a nucleotide sequence complementary thereto.

4. A replication and expression vector comprising the isolated DNA molecule of any one of claims 1 to 3.

5. A host cell which has been transformed or transfected with a replication and expression vector, wherein the vector comprises the DNA molecule of any one of claims 1 to 3.

6. A method of producing a SDF-1α polypeptide comprising the steps of:
    (a) culturing host cells which have been transformed or transfected with a replication and expression vector, wherein the vector comprises an isolated DNA molecule having a nucleotide sequence of SEQ ID NO:2 or SEQ ID NO:3, under conditions suitable to express a polypeptide; and
    (b) recovering the polypeptide.

7. An isolated DNA molecule encoding a Stromal Derived Factor-1β (SDF-1β) polypeptide having the amino acid sequence shown in SEQ ID NO:5.

8. An isolated DNA molecule comprising a DNA molecule having the nucleotide sequence shown in SEQ ID NO:6 or a nucleotide sequence complementary thereto.

9. An isolated DNA molecule comprising a DNA molecule having the nucleotide sequence shown in SEQ ID NO:7 or a nucleotide sequence complementary thereto.

10. A replication and expression vector comprising the isolated DNA molecule of any one of claims 7 to 9.

11. A host cell which has been transformed or transfected with a replication and expression vector, wherein the vector comprises the DNA molecule of any one of claims 7 to 9.

12. A method of producing a SDF-1β polypeptide comprising the steps of:
    (a) culturing host cells which have been transformed or transfected with a replication and expression vector wherein the vector comprises an isolated DNA molecule having a nucleotide sequence consisting of SEQ ID NO:6 or SEQ ID NO:7, under conditions suitable to express a polypeptide; and
    (b) recovering the polypeptide.

\* \* \* \* \*